United States Patent [19]  
Burkhardt et al.

[11] 4,098,933  
[45] Jul. 4, 1978

[54] PROCESS FOR THE PRODUCTION OF WATER-SOLUBLE OR WATER-DISPERSIBLE BLOCKED POLYISOCYANATES

[75] Inventors: Tilo Burkhardt; Kuno Wagner; Kurt Findeisen, all of Leverkusen, Germany

[73] Assignee: Bayer Aktiengesellschaft, Leverkusen, Germany

[21] Appl. No.: 630,112

[22] Filed: Nov. 10, 1975

[30] Foreign Application Priority Data

Nov. 29, 1974 [DE] Fed. Rep. of Germany ....... 2456469

[51] Int. Cl.² .............................................. B05D 3/02
[52] U.S. Cl. .............................. 427/379; 260/29.2 TN; 427/365 R; 528/45
[58] Field of Search .................. 427/379, 340, 385 R; 260/2 EP, 29.2 TN, 78 R, 75 TN, 75 NT, 77.5 TB

[56] References Cited

U.S. PATENT DOCUMENTS

| 3,384,506 | 5/1968 | Elkin ................................... 427/377 |
| 3,438,940 | 4/1969 | Keberle et al. ............... 260/29.2 TN |
| 3,514,316 | 5/1970 | Kemp et al. ......................... 427/340 |
| 3,773,729 | 11/1973 | Wakimoto et al. ........... 260/77.5 TB |
| 3,883,483 | 5/1975 | Anderson et al. ............. 260/77.5 TB |
| 3,897,377 | 7/1975 | Broecker et al. ............. 260/77.5 TB |
| 3,904,796 | 9/1975 | Zorn et al. ......................... 427/390 R |
| 3,933,759 | 1/1976 | Hoeschele ......................... 260/75 NT |
| 3,939,222 | 2/1976 | Dieterich ............................ 427/340 |

*Primary Examiner*—Ronald H. Smith  
*Assistant Examiner*—Janyce A. Bell  
*Attorney, Agent, or Firm*—Gene Harsh; Lawrence S. Pope; Frederick H. Colen

[57] ABSTRACT

This invention relates to a process for producing stable water dispersible blocked polyisocyanates, the compounds so produced and their use in producing coatings and films. These compounds are produced by blocking about 50 to 99.8 weight % of the isocyanate groups of an organic polyisocyanate and then reacting the partially blocked polyisocyanate with a compound carrying both an isocyanate reactive hydrogen and a hydrophilic group, e.g. a carboxylic acid salt or polyethylene oxide or a group convertible to a hydrophilic group, e.g. a carboxylic acid or tertiary amine. The blocked polyisocyanate with hydrophilic groups may then be dispersed in water with organic compounds having at least two isocyanate reactive hydrogen atoms per molecule and then cured by driving off the water and raising the temperature sufficiently high to unblock the polyisocyanate.

9 Claims, No Drawings

PROCESS FOR THE PRODUCTION OF WATER-SOLUBLE OR WATER-DISPERSIBLE BLOCKED POLYISOCYANATES

FIELD OF THE INVENTION

This invention relates to a process for the production of water-soluble or water-dispersible blocked polyisocyanates, to the compounds obtainable by this process and to the use thereof in the manufacture of sheet-form materials.

BACKGROUND OF THE INVENTION

Polyurethane dispersions of high molecular weight polyurethanes have been known for some considerable time and are acquiring increasing commercial significance because they enable polyurethanes to be applied without difficulty from aqueous medium [Angew. Makromolekulare Chemie, 26 (1972), pp. 85–106; Angew. Chemie, 82 (1970), pp. 53–90; Adv. in Urethane Science and Technology, Vol. 2, 109 (1973)]. Drying is accompanied solely by the evaporation of water, with the result that film- and sheet-forming systems of this type are environmentally acceptable. Conventional polyurethane dispersions are normally dispersed macromolecules whose hydrophilic components, ionic groups or non-ionic water-dispersing polyethylene oxide segments have been incorporated during synthesis of the polymers.

Hitherto, there have been no reports of stable solutions or dispersions of low molecular weight blocked polyisocyanates which would be suitable for use in the production of polyurethanes. Accordingly, it would be of considerable commercial interest to obtain aqueous solutions or dispersions of low molecular weight blocked polyisocyanates, because aqueous solutions or dispersions of this type would lend themselves to practically every application for which solutions of blocked polyisocyanates in organic solvents have hitherto been used. In conjunction with water-soluble or water-dispersible compounds containing isocyanate-reactive hydrogen atoms, the aqueous solutions or dispersions of blocked polyisocyanates could be used in particular for the production of coatings, films and impregnations. By using solutions or dispersions of blocked polyisocyanates of the type in question as additives to aqueous polyurethane dispersions, it would be possible to control the properties of the aqueous polyurethane dispersions, for example, the degree of swelling, wet strength or resistance to chemicals of the sheet-form materials produced there from by the action of heat.

The present invention provides a route to new water-soluble or water-dispersible blocked polyisocyanates. The solutions or dispersions of the blocked polyisocyanates in water are completely stable over a period of at least 3 months.

SUMMARY OF THE INVENTION

The present invention relates to a process for the production of water-soluble or water-dispersible blocked polyisocyanates characterized in that from about 50 to 99.8% of the isocyanate groups of an organic polyisocyanate are converted into a partially blocked polyisocyanate by reaction with a blocking agent in known manner, after which the thus-obtained partially blocked polyisocyanate is reacted with a compound which contains at least one hydrogen atom reactive to isocyanate groups and at least one hydrophilic group responsible for the solubility or dispersibility of the reaction product in water or at least one group which can be converted into a hydrophilic group of this type. In the latter case, the group which can be converted into a hydrophilic group is converted into a hydrophilic group on completion of the isocyanate addition reaction.

Accordingly, the invention also relates to the blocked polyisocyanates obtainable by this process.

Finally, the invention also relates to the use of the blocked water-soluble or water-dispersible polyisocyanates obtainable by this process, in the form of their aqueous solution or dispersion, in conjunction with aqueous solutions or dispersions of organic compounds containing at least two isocyanate-reactive hydrogen atoms, and optionally in conjunction with other auxiliaries and additives, for the production of sheet-form materials by coating suitable substrates with the combined aqueous solutions or dispersions removing the water and simultaneously or subsequently cross-linking the thus-obtained coating by the action of heat.

DETAILED DESCRIPTION OF THE INVENTION

The fact that the blocked isocyanates obtainable by the process according to the invention form stable solutions or dispersions in water is surprising insofar as it had been expected that blocked polyisocyanates in particular, reacted with blocking agents, such as malonic acid diethyl ester or acetoacetic acid ethyl ester, would not remain stable in aqueous medium, but instead would gradually react with the water to form polyureas, the reaction being accompanied by liberation of the blocking agent and also by the elimination of carbon dioxide.

Surprisingly, this is not the case. On the contrary, the solutions or dispersions of the products obtained by the process according to the invention in water show outstanding stability in storage.

Any organic polyisocyanates may be used for the process according to the invention. It is preferred to use di- or tetra-functional polyisocyanates with aliphatically and/or cycloaliphatically bonded isocyanate groups and a molecular weight of below about 800. Polyisocyanates particularly preferred for use in the process according to the invention are tris-(isocyanatohexyl)-biuret polyisocyanate, optionally in admixture with its higher homologues, obtainable, for example, in accordance with German Offenlegungsschrift No. 2,308,015 and U.S. Pat. No. 3,903,127 or polyisocyanate mixtures containing N-formyl urea groups of the type obtainable in accordance with German patent application No. P 24 37 130.0 and U.S. patent application Ser. No. 598,106, filed July 22, 1975. Other polyisocyanates which are particularly suitable for use in the process according to the invention are, for example, the reaction products of 1-isocyanato-3,3,5-trimethyl-5-isocyanatomethyl cyclohexane with deficits of low molecular weight polyols, such as, in particular, trimethylol propane.

The corresponding reaction products of hexamethylene diisocyanate with deficits of low molecular weight polyols, such as, in particular, trimethylol propane, are also suitable for use in the process according to the invention. Polyisocyanates containing urethane groups of this type are generally prepared by reacting the low molecular weight polyol with a large excess of the diisocyanate, and subsequently removing unreacted diisocyanate, for example by distillation. Bis-(6- isocyanatohexyl)-uretdione or polyisocyanates with isocyanurate groups of the type obtainable by trimerizating hexamethylene diisocyanate, optionally in admixture with 2,4-diisocyanato toluene, are also suitable for use in the process according to the invention. In addition to these preferred polyisocyanates, it is also possible to use, for the process according to the invention, any other aliphatic, cycloaliphatic, araliphatic, aromatic, or heterocyclic polyisocyanates, for example the type described by W. Siefken in Liebigs Annalen der Chemie 562, pages 75-136, such as ethylene diisocyanate, 1,4-tetramethylene diisocyanate, 1,6-hexamethylene diisocyanate, 1,2-dodecane diisocyanate, cyclobutane-1,3-diisocyanate, cyclohexane-1,3- and -1,4-diisocyanate, also mixtures of these isomers, 1-isocyanato-2-isocyanatomethyl cyclopentane, 1-isocyanato-3,3,5-trimethyl-5-isocyanatomethyl cyclohexane, 2,4- and 2,6-hexahydro tolylene diisocyanate and mixtures of these isomers, hexahydro-1,3- and/or -1,4-phenylene diisocyanate, perhydro-2,4'- and/or -4,4'-diphenyl methane diisocyanate, 1,3- and 1,4-phenylene diisocyanate, 2,4- and 2,6-tolylene diisocyanate and mixtures of these isomers, diphenyl methane-2,4'- and/or -4,4'-diisocyanate, naphthalene-1,5-diisocyanate, triphenyl methane-4,4',4''-triisocyanate, polyphenyl polymethylene polyisocyanates of the type obtained by condensing aniline with formaldehyde, followed by phosgenation, and mixtures of the above-mentioned polyisocyanates. Heterocyclic polyisocyanates such as for example 4,5-dichloro-2,6-diisocyanato pyrimidine may also be used.

Blocking agents suitable for use in the process according to the invention are, in particular, compounds with preferably one isocyanate-reactive group which enter into an addition reaction with organic isocyanates at temperatures above about 50° C and preferably at temperatures in the range of from about 60° to 100° C, and whose resulting addition products, in admixture with involatile polyols containing primary hydroxyl groups, react with the involatile polyols to form urethanes at temperatures in the range of from about 100° to 200° C, the reaction being accompanied by liberation of the blocking agent. Suitable blocking agents of this type are, for example, secondary or tertiary alcohols, such as isopropanol or tert.-butanol, C-H-acid compounds, such as malonic acid dialkyl esters, acetyl acetone, acetoacetic acid alkyl esters, oximes, such as formaldoxime, acetaldoxime, methyl ethyl ketone oxime, cyclohexanon oxime, acetophenone oxime, benzophenone oxime or diethyl glyoxime, lactams, such as E-caprolactam, δ-valerolactam, γ-butyrolactam, phenols, such as phenol, o-methyl phenol, N-alkyl amides, such as N-methyl acetamide, imides, such as phthalimide, imidazole or alkali metal bisulphites. C-H-acid compounds, more especially compounds containing activated methylene groups, such as malonic acid dialkyl esters with $C_1$-$C_4$-alkyl groups, especially malonic acid diethyl ester, acetoacetic acid alkyl ester with a $C_1$-$C_4$-alkyl radical, more especially acetoacetic acid ethyl ester or acetyl acetone, are preferably used in the process according to the invention.

The following are examples of compounds with at least one group which can be converted into a hydrophilic group, which are suitable for use in the process according to the invention:

1. Aliphatic hydroxy carboxylic acids with a molecular weight of below about 300, aliphatic or aromatic aminocarboxylic acids with primary or secondary amino groups and a molecular weight of below about 300, aliphatic hydroxy sulphonic acids with a molecular weight of below about 300 or aliphatic or aromatic aminosulphonic acids with primary or secondary amino groups and a molecular weight of below about 300, and the alkali metal salts, more especially the sodium or potassium salts, of these acids. It is preferred to use those representatives of the above-mentioned compounds which contain an isocyanate-reactive group and one or two acid or salt groups, the above-mentioned acid groups not really counting as "isocyanatereactive groups" on account of their sluggish reaction with isocyanate groups. The alkali metal salts of the above-mentioned compounds are used in preference to the free acids in the process according to the invention. In cases where the free acids are used, the acid groups are converted into the corresponding salt-like groups on completion of the isocyanate addition reaction by subsequent neutralization, for example with sodium hydroxide, potassium hydroxide, sodium carbonate, potassium carbonate, sodium bicarbonate or potassium bicarbonate, or even with organic phases, such as triethyl amine. Examples of suitable compounds of this type, which may optionally be used in their salt form, are taurine, N-methyl taurine, N-butyl taurine, 6-amino-caprioc acid, glycine, N-methyl glycine, sulphanilic acid, ornithine, lysine, 4-aminobutyric acid, β-alanine, 1,1-adducts of sultones, such as propane sultone or butane sultone, with diamines, such as ethylene diamine, hydrazine or hexamethylene diamine, 6-hydroxy caproic acid, dimethylol propionic acid, 4-hydroxy butane sulphonic acid or 4-aminobenzoic acid.

2. Tertiary amines with an aliphatically-bonded hydroxyl group and a molecular weight of below about 300, such as N,N-dimethyl ethanolamine, N,N-diethyl propanolamine or N,N-dimethyl propanolamine. In the process according to the invention, the tertiary nitrogen atoms of these compounds are generally converted into the corresponding ammonium groups on completion of the isocyanate addition reaction by reaction with an acid, for example hydrochloric acid, or an alkylating agent, for example methyl iodide, dimethyl sulphate or ethyl bromide, in known manner.

3. Monohydroxy polyalkylene oxides with molecular weights in the range of from about 500 to 5000 of the type which may be obtained in known manner by alkoxylating monofunctional starter molecules, for example monohydric alcohols, such as methanol, ethanol, propanol or butanol, and from about 50 to 100% of whose polyalkylene oxide chain is made up of ethylene oxide units and which, in addition to ethylene oxide units, preferably contain only propylene oxide units. The corresponding pure polyethylene oxides with terminal hydroxyl group are particularly preferred.

The process according to the invention is preferably carried out as follows:

The starting polyisocyanate is preferably reacted at a temperature above about 50° C, preferably at a temperature in the range of from about 60° to 100° C, with a quantity of blocking agent which corresponds to a ratio of NCO-groups to NCO-reactive groups of from about 1 : 0.5 to 1 : 0.998, preferably from about 1 : 0.85 to 1 : 0.95. However, it is also possible in principle to use an excess of blocking agent and to stop the blocking reaction at the required degree of blocking of from about 50 to 99.8%, preferably from about 85 to 95%, of the isocyanate groups originally present, by cooling to room temperature. In such a case, the excess blocking agent is generally removed by distillation on completion of the reaction of the partically blocked isocyanate with the hydrophilic components. It may generally be assumed that the blocking agents containing activated methylene groups preferably used for the process according to the invention also represent monofunctional blocking agents. The blocking reaction is usually carried out in the absence of a solvent. It is advisable to carry out the blocking reaction in the presence of a catalyst, depending upon the type of blocking agent used. In cases where alcohols are used as blocking agent, it is advisable to use a metal catalyst, for example dibutyl tin dilaurate. In cases where the preferred blocking agents containing activated methylene groups are used, it is advisable to use basic catalysts, such as diazabicyclooctane, triethyl amine, alkali metal alcoholates or alkali metal phenolates, such as sodium phenolate. The catalysts are used in quantities of from about 0.05 to 0.5%, by weight, based on the reaction mixture as a whole.

The free isocyanate groups still present on completion of the blocking reaction are reacted with the hydrophilic components in a second reaction stage. The hydrophilic components are preferably used in such a quantity that there is at least one NCO-reactive group of the hydrophilic components for every isocyanate group still present. Reaction of the partially blocked polyisocyanate with the hydrophilic components may be carried out in the presence or even in the absence of solvents. It is preferred to use water-miscible solvents boiling at temperatures in the range of from about 40° to 90° C, such as acetone or methyl ethyl ketone. In one embodiment of the process according to the invention for example, solutions of the partially blocked polyisocyanate and the reaction components containing the hydrophilic group are combined at room temperature or moderately elevated temperature (the hydrophilic component may also be added as such to the solution of the partially blocked polyisocyanate), and kept at a moderately elevated temperature, for example at a temperature in the range of from about 20° to 90° C, until the addition reaction is over. On completion of the reaction, the dissolved end product may either be obtained as such by distilling off the solvent and any unreacted blocking agent still present, or, if there is no need to remove excess blocking agent, may be converted into an aqueous dispersion by stirring the solution into water and subsequently distilling off the solvent.

In another embodiment of the process according to the invention, the partially blocked polyisocyanate present in organic solution is combined with an aqueous solution of the hydrophilic reaction components and heated to from about 20° to 90° C until the addition reaction is over. If there is no need in this embodiment to remove excess blocking agent, an aqueous solution or dispersion of the end product according to the invention is directly obtained by distilling off the solvent. However, if it is necessary to remove unreacted blocking agent, it is advisable to distil off in vacuo water, organic solvent and excess blocking agent, to takeup end product according to the invention left as residue in a suitable solvent, for example acetone, and to convert this acetone solution into the aqueous dispersion or solution in the same way as described above following the addition of water and removal of the acetone by distillation. In this embodiment of the process according to the invention, it is preferred to use hydrophilic reaction components containing primary and/or secondary amino groups as the NCO-reactive groups.

In another embodiment of the process according to the invention, it is even possible to work in the absence of solvents especially when the hydrophilic components mentioned in (3) above are used. In this case, the hydrophilic component mentioned in (3) above is combined as such with the partially blocked polyisocyanate at moderately elevated temperature (for example from 30° to 70° C) and left to react. The reaction mixture is then combined with the requisite quantity of water to convert the product obtained in this way into an aqueous solution or dispersion.

The exemplary embodiments of the process according to the invention as described above relate to the use of hydrophilic reactants in which the hydrophilic groups are already present before the reaction with the partially blocked polyisocyanate. In cases where the above-mentioned hydroxy or amino acids are used, they are preferably converted into the salt form by adding the bases mentioned by way of example above to the aqueous system, or where organic amines, for example triethyl amine, are used, also by neutralizing the acid groups in organic phase. The compounds containing tertiary amino groups mentioned in (2) above may be used in particular in the first embodiment of the process according to the invention. The tertiary amino nitrogen atoms are converted into the corresponding ammonium ions either by quaternization in the solvent phase or by the addition of suitable acids to the aqueous system.

As already mentioned, the end products obtained by the process according to the invention are compounds which can be dissolved or dispersed in water. The question of whether the end products obtained by the process according to the invention are present in water in the form of a solution or rather in the form of a dispersion, is primarily governed by the intensity of stirring during conversion of the organic phase into the aqueous phase or during combination of the organic solution of the partially blocked polyisocyanate with the hydrophilic reactant present in aqueous solution. Basically, it is also possible to modify the process according to the invention to the extent that, after the isocyanate groups of the starting polyisocyanate has been partially blocked, some of the remaining free isocyanate groups are reacted with hydrophilic reactant of the type mentioned in (3) above, while the rest of the free isocyanate groups are reacted with an ionic component or with a component which can be converted into an ionic component of the type mentioned in (1) or (2) above.

The presence of an organic solvent during the reaction of the partially blocked polyisocyanate with the hydrophilic components or during the conversion of the end products according to the invention into their aqueous solution or dispersion, is not absolutely essential if the partially blocked polyisocyanate or the end product according to the invention has a liquid consistency.

To convert the end products according to the invention into their aqueous solution or dispersion, water is generally used in such quantities that the solutions or dispersions have a solids content of from about 30 to 70%, by weight.

The aqueous solutions or dispersions of the end products according to the invention may be processed in combination with suitable reactants, for example the known aqueous polyurethane dispersions or even polyacrylate dispersions with isocyanate-reactive hydrogen atoms or even in combination with low molecular weight polyamines dissolved in water as thermo-crosslinkable coating compositions which can be processed from the aqueous phase. It is also possible to use the aqueous solutions or dispersions of the end products obtained by the process according to the invention without adding another reactant, for example for impregnating substrates containing isocyanate-reactive hydrogen atoms.

It can also be of advantage to add to the dispersions reactive carbonyl compounds, low molecular weight N-methylol compounds, aminoplast and phenoplast precondensates and to convert blocking agents released in this way into relatively high molecular weight components which neither interfer with formation of the film, nor exert any plasticizing effect, and hence to increase the degree of crosslinking.

Formaldehyde, dimethylol urea, trimethylol melamine, hexamethylol melamine, etherified methylolated melamines and bis-alkoxy methyl urea, are preferably used for this purpose.

During heating, the water is first evaporated, the crosslinking reaction beginning after the reforming temperature of the blocked polyisocyanate has been reached.

It is possible in this way to obtain non-tacky films and coatings, which may be used for a variety of different applications. The coatings may be obtained by coating the desired substrate, while free standing films are obtainable by coating a release support from which the cured film can be removed.

The following Examples illustrate preferred embodiments of the invention, although the invention is by no means limited to these particular embodiments.

EXAMPLE 1

A 3 liter capacity stirrer-equipped reaction vessel, equipped with an internal thermometer, stirrer, dropping funnel and gas inlet pipe, is filled with 294.7 g (2.27 mols) of acetoacetic acid ethyl ester. 0.69 g of sodium phenolate are added at room temperature and dissolved by stirring. 400 g of biuretized hexamethylene diisocyanate (23.8%, by weight, NCO $\doteq$ 2.267 NCO-equiv.) are run into the nitrogen-covered solution. An exothermic reaction begins, increasing the reaction temperature from 25° C to about 90° C. This temperature is maintained for 1 hour. After cooling to room temperature, 100 cc of acetone are added. Titrimetric determination of the free NCO-groups still present gives a value of 1.5%, by weight, of NCO $\doteq$ 0.283 NCO-equivalents, based on the total weight. 121.5 g of a 36.7% solution of the sodium salt of N-methyl aminoethane sulphonic acid in water are added dropwise to this solution. A weekly exothermic reaction takes place. The reaction mixture is stirred for 2 hours at 50° C. The solvent, acetone, and unreacted acetoacetic acid ethyl ester are removed by distillation, initially under a water jet pump vacuum for 2 hours, and then for 6 hours in an oil pump vacuum. The bath temperature should not exceed 70° C. The highly viscous residue is then redissolved in 200 cc of acetone and 1 liter of water added at a high stirring speed. The acetone is then removed again in water jet pump vacuum. The dispersion obtained is stable in storage for more than 3 months.

EXAMPLE 2

A 3 liter stirrer-equipped reaction vessel, equipped with an internal thermometer, stirrer, dropping funnel and gas inlet pipe, is filled with 288 g (1.8 mols) of malonic acid diethyl ester. Nitrogen is then admitted as protective gas, and 2.35 g of sodium phenolate dissolved in the malonic ester. 300 g of biuretized hexamethylene diisocyanate (23.8%, by weight, of NCO = 1.7 NCO-equivalents) are added to the solution at room temperature. After the exothermic reaction has abated, the temperature has risen to 75° C. After heating to 90° C, the reaction mixture is stirred for 2 hours at that temperature. It is then cooled to room temperature and its NCO-content determined after 100 cc of acetone have been stirred in. The solution is found to have an NCO-content of 0.55%, by weight = 90 m equivalents of NCO, based on total weight. 39.6 g of a 36.7% solution of the sodium salt of N-methyl aminoethane sulphonic acid in water (1 m equivalent - NH = 0.438 g of solution) are then added dropwise to this solution, followed by stirring for 2 hours at 50° C. The excess of unreacted malonic ester and the acetone are removed by distillation in the same way as in Example 1. The residue is dissolved in 200 cc of acetone, after which 1 liter of water is stirred in. The acetone is then removed from the dispersion again by distillation.

EXAMPLE 3

3 g of sodium phenolate are dissolved under nitrogen in 366 g of malonic acid diethyl ester (2.29 mols) in a 3 liter stirrer-equipped reaction vessel equipped with an internal thermometer, stirrer, dropping funnel and gas inlet pipe. 400 g of biuretized hexamethylene diisocyanate (24% by weight of NCO $\doteq$ 2.29 equivalents of NCO) are added dropwise to this solution. After the exothermic reaction abated, the reaction mixture is stirred for 20 minutes at 90° C, 250 cc of acetone being stirred in after cooling to room temperature. 100 g of an n-butanol-started polyethylene oxide alcohol of molecular weight 2000 ($\doteq$ 0.05 OH-equivalents) are then added to 960 g of this solution which has an NCO-content of 0.85% by weight ($\doteq$ 0.194 NCO-equivalents), as determined by titration, followed by stirring for 3 hours at 60° C after the addition of 0.1 g of dibutyltin dilaurate. The NCO-content falls to 0.277% by weight of NCO. 32.5 g of a 42.1% solution of the sodium salt of N-methyl aminoethane sulphonic acid in water are then added to 942 g of this solution with an NCO-content of 0.277% by weight, followed by stirring for 2 hours at 50° C. Acetone and the excess of malonic acid diethyl ester are then removed by distillation in the same way as described in Example 1. The viscous residue is dissolved in 200 cc of acetone, after which 1 liter of Lewatit water is stirred in. A storable dispersion of the blocked isocyanate is obtained after the acetone has been distilled off.

EXAMPLE 4

2 g of sodium phenolate are dissolved under nitrogen in 244.8 g (1.53 mols) of malonic acid diethyl ester in a 3 liter stirrer-equipped reaction vessel fitted with an internal thermometer, stirrer, dropping funnel and gas inlet pipe. 300 g of biuretized hexamethylene diisocyanate (23.8% by weight of NCO $\doteq$ 1.70 NCO-equivalents) are added to this solution. After the exothermic reaction has abated, the reaction mixture is stirred for 15 minutes at 90° C and its NCO-content determined by titration after cooling to room temperature. The titration value of 0.97% by weight of NCO corresponds to 0.126 NCO-equivalents, based on total weight. 100 cc of acetone are stirred into the reaction product, followed by the dropwise addition of 48.2 g of a 42.1% aqueous solution of the sodium salt of N-methyl aminoethane sulphonic acid. After stirring for 2 hours at 50° C, 1 liter of Lewatit water is stirred in. Acetone is removed again by distillation, leaving behind a storable aqueous dispersion of the blocked polyisocyanate.

EXAMPLE 5

2 g of sodium phenolate are dissolved under nitrogen in 190.4 g (1.19 mol) of malonic acid diethyl ester in a 3 liter stirrer-equipped reaction vessel fitted with an internal thermometer, stirrer, dropping funnel and gas inlet pipe. 300 g of biuretized hexamethylene diisocyanate (23.8% by weight of NCO $\doteq$ 1.7 NCO-equivalents) are added to this solution. After the exothermic reaction has abated, the reaction mixture is stirred for 6 hours at 90° C, after which NCO-titration gives a value of 1.88%, by weight $\doteq$ 0.22 NCO-equivalents, based on the total weight. After 150 cc of acetone have been stirred in, 84.1 g of an aqueous 42.1% solution of the sodium salt of N-methyl aminoethane sulphonic acid (1 m equivalent — NH — =0.3824 g of solution) are added, followed by stirring for 2 hours at 50° C. 1 liter of Lewatit water is stirred into this solution, the acetone removed by distillation in a water jet pump vacuum and a storable aqueous dispersion of the blocked polyisocyanate thus obtained.

EXAMPLE 6

2.2 g of sodium phenolate are dissolved under nitrogen in 237.8 g (1.49 mols) of malonic acid diethyl ester in a 3 liter stirrer-equipped reaction vessel fitted with an internal thermometer, stirrer, dropping funnel and gas inlet pipe. 300 g of a biuretized hexamethylene diisocyanate containing N-formyl urea groups (23.1% by weight of NCO $\doteq$ 1.65 NCO-equivalents) are added to this solution. After the exothermic reaction has abated, the reaction mixture is heated to 90° C and stirred for 10 minutes. After cooling, titration gives an NCO-value of 0.5% by weight, $\doteq$ 0.064 NCO-equivalents, based on the total weight.

100 cc of acetone are stirred in, followed by the addition of 24.48 g of a 42.1% aqueous solution of the sodium salt of N-methyl aminoethane sulphonic acid (1 m equivalent — NH — = 0.3824 g of solution). After stirring for 2 hours at 50° C, 1 liter of Lewatit water is stirred in and the acetone removed by distillation. A storable aqueous dispersion of the blocked isocyanate is obtained.

EXAMPLE 7

2.2 g of sodium phenolate are dissolved under nitrogen in 244.8 g of malonic acid diethyl ester (1.53 mol) in a 3 liter stirrer-equipped reaction vessel fitted with an internal thermometer, stirrer, dropping funnel and gas inlet pipe. 300 g of biuretized hexamethylene diisocyanate (23.8% by weight of NCO = 1.7 NCO-equivalents) are added under nitrogen to this solution. After the exothermic reaction has abated, the reaction mixture is stirred for 30 minutes at 90° C. After cooling titration reveals an NCO-content of 1.18%, by weight = 0.153 NCO-equivalents, based on the total weight. 100 cc of acetone are stirred into the mixture, followed by the addition of 60.4 g of a 28.1% aqueous solution of the sodium salt of N-methyl aminoacetic acid (1 m equivalent —NH —= 0.395 g of solution). After stirring for 2 hours at 50° C, 1 liter of Lewatit water is added with vigorous stirring. Removal of the acetone by distillation leaves a storable aqueous dispersion.

EXAMPLE 8

177.4 g of caprolactam (1.57 mol) are stirred under nitrogen into 300 g of biuretized hexamethylene diisocyanate containing N-formyl urea groups (23.1% by weight of NCO $\doteq$ 1.65 NCO-equivalents) in a 3 liter capacity stirrer-equipped reaction vessel fitted with an internal thermometer, stirrer, dropping funnel and gas inlet pipe. After heating to 110° C, the reaction mixture is stirred for 4 hours at that temperature. Thereafter NCO-determination reveals a value of 1.16% by weight of NCO $\doteq$ 0.132 NCO-equivalents, based on the total weight. After 200 cc of acetone have been added, 50.5 g of a 42.1% aqueous solution of the sodium salt of N-methyl aminoethane sulphonic acid (1 m equivalent — NH — = 0.3825 g of solution) are added, followed by stirring for 2 hours at 50° C. 1 liter of Lewatit water is then stirred in and the acetone distilled off, leaving behind a storable dispersion.

EXAMPLE 9

2.2 g of sodium phenolate are dissolved under nitrogen in 326.9 g of malonic acid diethyl ester (2.04 mol) in a 3 liter stirrer-equipped reaction vessel fitted with an internal thermometer, stirrer, dropping funnel and gas inlet pipe. 400 g of biuretized hexamethylene diisocyanate (23.8% by weight of NCO $\doteq$ 2.27 NCO-equivalents) are run into the solution. After the exothermic reaction has abated, the reaction mixture is stirred for 15 minutes at 90° C. Thereafter NCO-measurement reveals a value of 1.3% by weight of NCO = 0.226 NCO-equivalents, based on the total weight. 200 cc of acetone are then stirred into the reaction mixture, followed by the addition of 452 g of an n-butanol-started polyethylene oxide alcohol (MW: 2000→2 g $\doteq$ 1 OH-m equivalent). The reaction is catalyzed with 0.5 g of dibutyl tin dilaurate and the reaction mixture stirred for 5 hours at 60° C. Thereafter no NCO-band is visible in the infrared spectrum. 1.5 liters of Lewatit water are stirred in and the acetone distilled off, leaving behind a storable aqueous dispersion of the blocked polyisocyanate.

EXAMPLE 10 (Application Example)

The dispersion prepared in accordance with Example 9 is applied with a brush to a grease-fire glass plate. The glass plate is then heated for 30 minutes at 80° C and for 60 minutes at 125° C, a tack-free film of outstanding transparency being obtained.

EXAMPLE 11 (Application Example)

A solution of 11.9 g of 1,1-bis-(4-aminocyclohexyl)-propane in 100 g of water is stirred into 100 g of the dispersion prepared in accordance with Example 4 (masked NCO-content: 0.99 NCO-equivalents per liter). A thin film of the mixture is coated onto a grease-free glass plate and heated in a drying cabinet first for 30 minutes at 80° C and then for 1 hour at 120° C. A transparent, tack-free film with excellent properties is obtained.

EXAMPLE 12

3 g of sodium phenolate are dissolved under nitrogen in 367.4 g of malonic acid diethyl ester (2.29 mols) in a 3 liter stirrer-equipped vessel fitted with an internal thermometer, stirrer and gas inlet pipe. 450 g of biuretized hexamethylene diisocyanate (23.8% by weight of NCO = 2.55 NCO-equivalents) are added, under nitrogen, to this solution. After the exothermic reaction has abated, the reaction mixture is stirred for 10 minutes at 90° C. After cooling, titration reveals an NCO-value of 3.6% by weight, based on the total weight. 480 g of an n-butanol-started polyethylene oxide alcohol (MW: 700, 0.7 g $\hat{=}$ 1 OH-m equivalent) are stirred into the mixture. The reaction is catalyzed with 0.5 g of dibutyl tin dilaurate and the reaction mixture stirred for 5 hours at 60° C. Thereafter, no NCO-band is visible in the infra-red spectrum. 1 liter of Lewatit water is then stirred into the warm, stirrable mass. A clear transparent solution of the blocked polyisocyanate is obtained.

EXAMPLE 13

173 g of caprolactam (1.53 mols) and 300 g of biuretized hexamethylene diisocyanate (23.8% by weight, of NCO = 1.7 NCO-equivalents) are combined under nitrogen and stirred for 4 hours at 90° C in a 3 liter stirrer-equipped vessel fitted with an internal thermometer, stirrer and gas inlet pipe. Subsequent NCO-titration reveals a value of 2.4% by weight of NCO = 0.27 NCO-equivalents. 270 g of an n-butanol-started polyethylene oxide alcohol (MW: 1000, 1 g $\hat{=}$ OH-m equivalent) are then stirred in. The reaction is catalyzed with 0.5 g of dibutyl tin dilaurate and the reaction mixture stirred for 2 hours at 90° C. Thereafter, no NCO-band is visible in the infra-red spectrum. 1 liter of Lewatit water is then stirred at 55° C into the warm, stirrable mass, giving a stable latex of the caprolactam-blocked polyisocyanate.

EXAMPLE 14

2 g of sodium phenolate are dissolved under nitrogen in 245 g of malonic ester (1.53 mols) in a 3 liter stirrer-equipped reaction vessel fitted with an internal thermometer, stirrer and gas inlet pipe. 300 g of biuretized hexamethylene diisocyanate (23.8% by weight of NCO = 1.7 NCO-equivalents) are added under nitrogen to this solution. After the exothermic reaction has abated, the reaction mixture is stirred for 30 minutes at 90° C. After cooling, titration reveals an NCO-content of 1.4% by weight = 0.182 NCO-equivalents, based on the total weight. 182 g of an n-butanol-started polyethylene oxide alcohol (MW: 1000 1 g $\hat{=}$ 1 OH-equivalent) are stirred into the mixture. The reaction is catalyzed with 0.5 of dibutyl tin dilaurate and the reaction mixture stirred for 5 hours at 60° C. 1 liter of Lewatit water is then stirred into the still warm, stirrable mass. A storable latex of the blocked polyisocyanate is obtained.

EXAMPLE 15

A mixture of 400 g of biuretized hexamethylene diisocyanate (23.6% by weight of NCO $\hat{=}$ 2.25 NCO-equivalent) with 229 g (2.05 mols) of ε-caprolactam is prepared in the reaction vessel of Example 1 and maintained at 90° C for 5 hours under a nitrogen atmosphere. Thereafter the NCO content was found to be 1.6% by weight of NCO which corresponds to a content of the reaction mixture of 0.24 NCO-equivalents. 16.1 g (0.12 mol) of dimethylolpropionic acid and 0.5 g of dibutyl tin dilaurate are subsequently added the reaction mixture which is in form of a melt. The mixture thus obtained is stirred for 4 hours at 100° C. Then a solution of 10.7 g (0.12 mole) of N,N-dimethylaminoethanol in 800 cm³ of water are added dropwise under stirring to the molten reaction mass at 100° C. Subsequently no NCO-edge can be detected in the IR spectrum. A storable stable aqueous dispersion of the blocked polyisocyanate is obtained.

EXAMPLE 16

235 g of a polyisocyanate obtained by reacting trimethylolpropane with a threefold molar quantity of 1-isocyanato-3,3,5-trimethyl-5-isocyanatomethyl-cyclohexane are mixed with 203 g (1.8 mol) of ε-caprolactam in a reaction vessel having a capacity of 3 liters and being equipped as the reaction vessel of the Example 1 and subsequently stirred for 4 hours at 100° C under nitrogen. Subsequently 175 g of a polyether alcohol obtained by ethoxylation of n-butanol and having an OH-number of 53.6 are added dropwise together with 0.5 g of dibutyl-tin dilaurate. The mixture is stirred at 100° C until no NCO-edge can be detected in the IR-spectrum. 700 cm³ of water are subsequently added dropwise at 100° C to the reaction mass under stirring. A storage stable aqueous dispersion of the blocked polyisocyanate is obtained.

EXAMPLE 17

300 g of a modified polyisocyanate obtained by reacting trimethylolpropane with an excess of hexamethylene diisocyanate and subsequent removal of unreacted hexamethylenediisocyanate in a thin-layer distillation apparatus (13.25% by weight of NCO which corresponds to 0.95 NCO-equivalents) are mixed with 96.7 g (0.85 mol) of ε-caprolactam in the reaction vessel of Example 16. Subsequently the reaction mixture is heated for 4 hours to 90° C under nitrogen. Subsequently 190.3 g of a polyether alcohol obtained by ethoxylation of n-butanol having an OH-number of 28 and 0.3 g of dibutyl tin dilaurate are added. The mixture is stirred at 90° C until no NCO-edge can be detected in the IR-spectrum. Subsequently 600 cm³ of water are added to the melt at 90° C. A storage stable aqueous dispersion of the blocked polyisocyanate is obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a water-soluble or water-dispersible blocked polyisocyanate, wherein from about 85 to 95% of the isocyanate groups of an organic polyisocyanate are converted into a partially blocked polyisocyanate in a known manner by reaction with a blocking agent selected from the group consisting of C-H-acid compounds and lactams, and the thus obtained partially blocked polyisocyanate is subsequently reacted with a compound which contains at least one isocyanate-reactive hydrogen atom and at least one hydrophilic group, or group which can be converted into a hydrophilic group, responsible for the solubility or dispersibility of the reaction product in water, said compound selected from the group consisting of i. aliphatic hydroxy carboxylic acids, with molecular weights of less than about 300, aliphatic or aromatic amino carboxylic acids with primary or secondary amino groups and molecular weights less than about 300, aliphatic hydroxy sulphonic acids with molecular weights less than about 300, aliphatic or aromatic aminosulphonic acids with primary or secondary amino groups and molecular weights less than about 300 and the alkali metal salts of these acids, ii. tertiary amines with aliphatically bound hydroxyl groups and molecular weights of less than about 300 and the corresponding ammonium salts of these tertiary amines, and iii. monohydroxy polyalkylene oxides with molecular weights of between about 500 and 5000 and at least about 50% ethylene oxide units, and said group convertible into a hydrophilic group, if present, being converted into a hydrophilic group on completion of the isocyanate addition reaction.

2. An embodiment of the process claimed in claim 1 in which preparation of the water-soluble or water-dispersible blocked copolymer is accompanied by its dissolution or dispersion in water, wherein the compound containing at least one isocyanate-reactive hydrogen atom and at least one hydrophilic group is reacted in the form of its aqueous solution with the partially blocked polyisocyanate.

3. Soluble or dispersible blocked polyisocyanates obtainable in accordance with claim 1.

4. The use of the water-soluble or water-dispersible blocked polyisocyanates obtainable in accordance with claim 1, in the form of their aqueous solution or dispersion, in combination with aqueous solutions or dispersions of organic compounds with at least two isocyanate-reactive hydrogen atoms and optionally in conjunction with other auxiliaries and additives, for the production of sheet-form materials by coating suitable substrates with the combined aqueous solutions or dispersions, removing the water and simultaneously or subsequently cross-linking the thus-obtained coating under the action of heat.

5. The process of claim 1 wherein the blocking agent is selected from the group consisting of malonic acid dialkyl esters with $C_1$–$C_4$ alkyl groups, acetoacetic acid dialkyl ester with a $C_1$–$C_4$ alkyl group and $\epsilon$-caprolactam.

6. A process for the production of water-dispersible blocked polyisocyanates which comprises (a) reacting at temperatures between about 60° and 100° C a di- to tetra-functional polyisocyanate with aliphatically and/or cycloaliphatically bound isocyanate groups having molecular weights less than about 800, with a blocking agent which has one isocyanate reactive group selected from the group consisting of C-H-acid compounds and lactams and whose bond with an isocyanate group is displaced by primary hydroxyl groups at temperatures between about 100° and 200° C at an NCO to blocking agent ratio of between about 1:0.85 to 1:0.95 to form a partially blocked polyisocyanate and then (b) reacting the partially blocked polyisocyanate with a compound selected from the group consisting of i. aliphatic hydroxy carboxylic acids, with molecular weights of less than about 300, aliphatic or aromatic amino carboxylic acids with primary or secondary amino groups and molecular weights less than about 300, aliphatic hydroxy sulphonic acids with molecular weights less than about 300, aliphatic or aromatic aminosulphonic acids with primary or secondary amino groups and molecular weights less than about 300 and the alkali metal salts of these acids, ii. tertiary amines with aliphatically bound hydroxyl groups and molecular weights of less than about 300, and the corresponding ammonium salts of these tertiary amines, and iii. monohydroxy polyalkylene oxides with molecular weights of between about 500 and 5000 and at least about 50% ethylene oxide units at an isocyanate reactive group to NCO group ratio of at least 1 and a temperature of between about 20° and 90° C and then of between about 20° and 90° C and then (c) in the case when acids are used neutralizing the acid group with an alkali metal base and in the case when tertiary amines are used converting said amino group to an ammonium group.

7. The process of claim 6 wherein the blocking agent is selected from the group consisting of malonic acid dialkyl esters with $C_1$–$C_4$ alkyl groups and acetoacetic acid alkyl ester with a $C_1$–$C_4$ alkyl group.

8. The water-dispersible blocked polyisocyanates produced by the process of claim 6.

9. A process for the production of cured sheet-form materials comprising (a) mixing a blocked water-dispersible or water-soluble polyisocyanate produced by the process of claim 1 in an aqueous solution of dispersion with organic compounds having at least two isocyanate reactive hydrogen atoms per molecule, (b) coating a suitable substrate with said aqueous solution or dispersion, and (c) removing the water and simultaneously or subsequently cross-linking the thus obtained coating under the action of heat.

* * * * *